United States Patent [19]

Chazono et al.

[11] Patent Number: 4,849,358
[45] Date of Patent: Jul. 18, 1989

[54] METHOD FOR CULTURING *BORDETELLA PERTUSSIS*, A PERTUSSIS TOXOID AND A PERTUSSIS VACCINE

[75] Inventors: Masashi Chazono; Iwao Yoshida; Takeo Konobe, all of Kanonzi; Juichiro Osame, Mitoyo; Keisuke Takaku, Suita, all of Japan

[73] Assignee: The Research Foundation for Microbial Diseases of Osaka University, Osaka, Japan

[21] Appl. No.: 73,134

[22] Filed: Jul. 14, 1987

[30] Foreign Application Priority Data

Apr. 24, 1987 [JP] Japan .................. 62-102360

[51] Int. Cl.⁴ ............................ C12N 1/22
[52] U.S. Cl. ..................... 435/252; 435/252.1; 435/252.5; 435/244; 435/248; 435/243; 435/68; 435/832; 424/88; 424/92
[58] Field of Search .......... 435/68, 243, 244, 252-253, 435/248, 832

[56] References Cited

U.S. PATENT DOCUMENTS

| | | | |
|---|---|---|---|
| 4,029,766 | 6/1977 | Helting | 424/92 |
| 4,247,452 | 1/1981 | Irons et al. | 424/92 |
| 4,455,297 | 6/1984 | Syukuda et al. | 424/92 |
| 4,500,639 | 2/1985 | Suzuki et al. | 435/244 |
| 4,551,429 | 11/1985 | Greenspan | 435/68 |
| 4,563,303 | 11/1986 | Ginnagan | 424/92 |
| 4,578,270 | 3/1986 | Csizer et al. | 424/92 |
| 4,687,738 | 8/1987 | Gunnoga et al. | 424/88 |
| 4,699,786 | 10/1987 | Lin et al. | 424/92 |
| 4,704,274 | 11/1987 | Sakuma et al. | 424/88 |
| 4,705,686 | 11/1987 | Scott et al. | 424/92 |
| 4,770,875 | 9/1988 | Kume et al. | 424/92 |
| 4,784,589 | 11/1988 | Robinson et al. | 424/92 |
| 4,788,058 | 11/1988 | Parton et al. | 424/92 |

FOREIGN PATENT DOCUMENTS

| | | |
|---|---|---|
| 0004137 | 9/1979 | European Pat. Off. . |
| 0080021 | 6/1983 | European Pat. Off. . |
| 0121249 | 10/1984 | European Pat. Off. . |
| 0140386 | 5/1985 | European Pat. Off. . |
| 0162639 | 11/1985 | European Pat. Off. . |
| 0175841 | 4/1986 | European Pat. Off. . |
| 2356429 | 1/1978 | France . |
| 56-47167 | 11/1981 | Japan . |
| 57-5203 | 1/1982 | Japan . |
| 58-222032 | 12/1983 | Japan . |
| 59-110626 | 6/1984 | Japan . |
| 59-175439 | 10/1984 | Japan . |
| 60-28277 | 7/1985 | Japan . |
| 60-218326 | 11/1985 | Japan . |
| 60-226822 | 11/1985 | Japan . |
| 60-237027 | 11/1985 | Japan . |
| 61-53224 | 3/1986 | Japan . |
| 62-5922 | 1/1987 | Japan . |

OTHER PUBLICATIONS

Bulletin of the World Health Organization 63 (2), 241-248, 1985.
Developments in Biological Standardization, 48, 207-234, 1981.
Journal of American Medical Association, 251 (2), 251, 1984.

*Primary Examiner*—Delbert R. Phillips
*Assistant Examiner*—Garnette D. Draper
*Attorney, Agent, or Firm*—Armstrong, Nikaido, Marmelstein, Kubovcik & Murray

[57] ABSTRACT

There is disclosed a method for culturing *Bordetella pertussis* in the presence of a cellulose and/or cellulose derivatives. The present method is useful for obtaining a mixed antigen comprising pertussis toxin and filamentous hemagglutinin in a large amount at low cost. From the antigen, there can be obtained a stable and effective pertussis toxoid to be used for a pertussis vaccine. There is also disclosed a vaccine comprising the pertussis toxoid as an active ingredient and a gelatin and/or gelatin derivatives as a stabilizing agent. The present vaccine is extremely stable and can be stored for a prolonged period of time.

2 Claims, No Drawings

METHOD FOR CULTURING *BORDETELLA PERTUSSIS*, A PERTUSSIS TOXOID AND A PERTUSSIS VACCINE

Background of The Invention

1. Field of the Invention

This invention relates to a method for culturing *Bordetella pertussis*. The present invention also relates to a pertussis toxoid. Further, the present invention is concerned with a vaccine comprising the pertussis toxoid as an active ingredient. The method of the present invention is advantageous for producing a culture which contains an increased amount of a mixed antigen comprising pertussis toxin and pertussis filamentous hemagglutinin. From the culture, the mixed antigen can easily be isolated. The pertussis toxoid of the present invention is readily obtained from the mixed antigen and, therefore, can be produced easily at low cost. The pertussis toxoid of the present invention is extremely effective as an active ingredient for a pertussis vaccine and a diagnostic agent for pertussis.

2. Discussion of Related Art

Pertussis is an acute respiratory infectious disease caused by the infection of *Bordetella pertussis*. The pertussis affects the bronchus and bronchiole and is characterized by explosive coughing ending in a whooping inspiration, which coughing is peculiar to the disease and is vulgarly said to last for a hundred days. In fact, the explosive coughing is caused repeatedly for several weeks. Particularly, in the case of an infant suffering from pertussis, an apnea-paroxysmal cough occurs and is sometimes accompanied with a spasm. For preventing this disease, in Japan, since 1949, the inoculation of pertussis vaccine to infants in early period after birth has been carried out. Conventional pertussis vaccines contain inactivated cells of the bacterium as an active ingredient and, therefore their inoculation tends to cause unfavorable side effects. As the side effects, there are well known, for example, various local reactions at the site of the inoculation of a pertussis vaccine, systemic symptoms such as fever, moroseness, vomiting and diarrhea, temporary nervous spasm and neurogenic shock, and severe encephalitis and the like. On the other hand, in recent years, the morbidity and mortality from pertussis have notably decreased due to the improvement of living conditions and the development of chemotherapies. Hence, nowadays, the above-mentioned side effects caused by the vaccine inoculation rather than the danger of infection with the disease have become a serious problem. However, it is very dangerous that the vaccination for pertussis is stopped in order to avoid those side effects. This is apparent from the past bitter experience that many infant patients died of pertussis in Japan and England owing to natural prevalence of pertussis which was caused by the temporary stop of vaccination. Accordingly, it is considered that the inoculation of pertussis vaccine is still important and necessary.

Heretofore, there have been reported many substances as a protective antigen, biologically active substance or component of *Bordetella pertussis*. As such substances, there may be mentioned, for example, a heat-labile toxin or a dermonecrotic toxin; a heat-labile agglutinogen; an endotoxin or a lipopolysaccharide; a filamentous hemagglutinin (F-HA); a histamine sensitizing factor (HSF); a leukocytosis or lymphocytosis promoting factor (LPF); a pertussis toxin (PT) which is also called lymphocytosis promoting factor hemagglutinin (LPF-HA); an adjuvant factor; an adenylate cyclase; an islet-activating factor; an outermembrane protein and the like. Of those substances, up to now, the filamentous hemagglutinin (hereinafter often referred to as "F-HA") and pertussis toxin (hereinafter often referred to as "PT") have been put to practical use as the active ingredient of a pertussis toxoid or a pertussis component vaccine.

As mentioned before, it is known that conventional vaccines have various side effects because the vaccines contain inactivated cells of the bacterium as an active ingredient. Accordingly, in all the world, it has strongly been desired to develop a safe and potent vaccine having a uniform quality without the above-mentioned side effects (Journal of American Medical Association 251(2), 251, 1984; Bulletin of the World Health Organization, 63(2), 241–248, 1985). In Japan, a pertussis toxoid (a purified adsorbed pertussis vaccine) which contains as an active ingredient a substance obtained by detoxifying a protective antigen fraction (F-HA and PT) derived from *Bordetella pertussis* has already been approved by the Ministry of Health and Welfare, Japan and has been marketed since Autumn 1981. With respect to the techniques for preparation of the vaccine, there are disclosed in, for example, Japanese Patent Publication No. 57-5203, U.S. Pat. Nos. 4,455,297, and 4,500,639, Japanese Patent Application Laid-Open Specification Nos. 58-222032, 59-175439, European Patent Application Laid-Open Specification Nos. 121249, 140386, Japanese Patent Application Laid-Open Specification Nos. 60-218326, 60-226822, Japanese Patent Publication No. 60-28277, Japanese Patent Application Laid-Open Specification Nos. 60-237027, 61-53224, European Patent Application Laid-Open Specification No. 175841, Japanese Patent Application Laid-Open Specification No. 62-5922, U.S. Pat. Nos. 4,029,766, 4,551,429, etc. Further, with respect to the preparation of a component vaccine by the use of a substance derived from *Bordetella pertussis* as an active ingredient, there are known, for example, the use of cell wall (Japanese Patent Publication No. 56-47167), the use of islet-activating factor (Japanese Patent Application Laid-Open Specification No. 59-110626), the use of outermembrane protein (European Patent Laid-Open Specification Nos. 4137, 80021), the use of a fraction having adenylate cyclase activity (European Patent Application Laid-Open Specification No. 162639), the use of an endotoxin (French Patent Application Laid-Open Specification No. 2356429), etc. However, the above-mentioned customary techniques each have at least one of the following disadvantages.

(1) The production cost is high because expensive materials are needed.

(2) The yield of an active ingredient for a vaccine is low.

(3) The safety, potency, uniformity in quality and stability of a vaccine produced is not satisfactory.

For Example, in U.S. Pat. No. 4,500,639, Japanese Patent Application Laid-Open Specification No. 59-175439, European Patent Application Laid-Open Specification No. 121249 and Japanese Patent Publication No. 60-28277 mentioned above, it is disclosed that in order to increase the yields of PT and F-HA, cyclodextrin which is known as a host compound capable of forming inclusion complexes is added to a basal medium for culturing *Bordetella pertussis*. However, this technique has the following disadvantages.

(1) Cyclodextrin to be used is expensive.
(2) The produced PT and F-HA are in the state included in the cyclodextrin in the medium and it is difficult to separate them from the cyclodextrin and highly purify them.

That is, such a technique is not economic because expensive materials and expensive purification apparatuses are needed and the procedures involved therein is very complicated and troublesome. Therefore, it is difficult to obtain a pertussis vaccine having safety and uniformity in quality. Further, in the above-mentioned U.S. Pat. No. 4,551,429, it is disclosed that a polyvinyl alcohol is added to a basal medium of *Bordetella pertussis* for the same purpose as described above. However, in this reference, there is no description of a method for purifying PT and F-HA to high degree and of the quality of the PT and F-HA produced and, therefore, it is questionable that the vaccine obtained according to this reference contains high purity PT and F-HA and is uniform in quality.

As is generally known, in 1979, WHO (World Health Organization) started an Expanded Programme on Immunization (EP) and is now carrying out this programme. The object of the programme is to give 6 kinds of vaccines in total, namely, pertussis vaccine, tetanus vaccine, diphtheria vaccine, tuberculosis vaccine, polio vaccine and measles vaccine to all the infants in the world until 1990 (WHO Chronicle, 36(4) 131-152, 1982). In order to fulfill this programme, the WHO urges to develop vaccines which are excellent in stability and heat resistance and can be used in the tropics in which refrigerators have not been spread, and put them to practical use [WHO Technical Report Series, No. 673, 15, (1982)]. Furthermore, vaccines of which the titers are not decreased even when they are frozen are also extremely useful because the vaccines are also used in cold districts. Therefore, in all the world, it has been expected to develop highly stable vaccines which are excellent in both heat resistance and cold resistance and, therefore, can be used at an atmospheric temperature in any of the tropics and the cold districts. With respect to heat-resistant vaccines, it is known, for example, dried vaccines such as a live virus vaccine, an inactivated virus vaccine, a mixed accellular vaccine comprising an inactivated bacterium and a toxoid (Japanese Patent Application Laid-Open Specification No. 59-19682) and the like. However, the above-mentioned dried vaccines are poor in stability such that after storage at 37° C. for about a month, the titers of them are decreased to degrees as low as 10 to 50% relative to the titers of the vaccines before the storage. Hence, it has been strongly desired to develop a vaccine which is extremely excellent in heat resistance and cold resistance and stable such that the titer of the vaccine is scarcely decreased even when preserved, for example, at a temperature of from about $-20$ C. to about 50° C. for several months.

Furthermore, a pertussis toxoid obtained by detoxifying a pertussis toxin using formalin is now available on the market, but such a toxoid has a serious disadvantage that the toxoid is apt to revert to a toxic state during the storage and, therefore, after the storage the safeness of the toxoid can no longer be assued. In order to prevent the above-mentioned reversion of the toxoid to a toxic state, it has been proposed that instead of formalin, carbodiimide is used as a detoxifying agent (Japanese Patent Application Laid-open Specification No. 62-5922). However, the use of carbodiimide is questionable because the safeness of carbodiimide has not been confirmed.

It is earnestly expected in the art to eliminate the above-mentioned drawbacks and disadvantages of the conventional vaccines and develop an improved pertussis vaccine.

SUMMARY OF THE INVENTION

The present inventors have made extensive and intensive studies to solve the above-mentioned problems. As a result, it has been found that when *Bordetella pertussis* is cultured in the presence of cellulose and/or a cellulose derivative, PT and F-HA can be produced in the culture in high yield at low cost and the thus obtained PT and F-HA can easily be purified from the culture. Further, it has been found that the pertussis toxoid obtained by detoxifying such PT and F-HA using formalin does not revert to a toxic state. Furthermore, it has been found that by adding a gelatin and/or a gelatin derivative to a vaccine containing the above-obtained pertussis toxoid as an active ingredient or a mixed vaccine containing the pertussis toxoid and an antigen other than the pertussis toxoid, the stability of the vaccine is extremely improved. Moreover, it has been found that by subjecting the above-mentioned vaccines to lyophilization, their stability is further improved. Based on the above-mentioned novel findings, the present invention has been completed.

It is, therefore, an object of the present invention to provide a novel method for culturing *Bordetella pertussis* which is effective for producing a mixed antigen comprising PT and F-HA used for preparing a pertussis vaccine can be produced in the culture of *Bordetella pertussis* in an increased amount at low cost.

It is another object of the present invention to provide a pertussis toxoid which can be used as a safe, stable and effective active ingredient for a pertussis vaccine.

It is a further object of the present invention to provide a pertussis vaccine which is excellent in heat resistance and cold resistance and can be stored at an atmospheric temperature for a prolonged period of time.

DETAILED DESCRIPTION OF THE INVENTION

Essentially, according to the present invention, there is provided a method for culturing *Bordetella pertussis* in a nutrient medium, characterized in that use is made of a nutrient medium containing at least one substance selected from the group consisting of cellulose and cellulose derivatives.

Also, according to the present invention, there is provided a mixed antigen comprising pertussis toxin and pertussis filamentous hemagglutinin, which is obtained by separating a culture obtained according to the above-mentioned method into a supernatant and cells of *Bordetella pertussis* and subjecting said supernatant to purification.

Further, according to the present invention, there is provided a pertussis toxoid obtained by detoxifying the above-mentioned mixed antigen.

Moreover, according to the present invention, there is provided an adsorbed pertussis vaccine comprising an effective immunogenic amount of the above-mentioned pertussis toxoid, said pertussis toxoid being adsorbed on an adjuvant, and at least one pharmaceutically acceptable carrier, diluent or excipient.

Furthermore, according to the present invention, there is provided an adsorbed pertussis vaccine comprising an effective immunogenic amount of the abovementioned pertussis toxoid, said pertussis toxoid being adsorbed on an adjuvant, at least one pharmaceutically acceptable carrier, diluent or excipient, and a stabilizing agent.

Furthermore, according to the present invention, there is provided a mixed vaccine which comprises effective immunogenic amounts of the abovementioned pertussis toxoid, said pertussis toxoid being adsorbed on an adjuvant, at least one antigen other than said pertussis toxoid, and at least one pharmaceutically acceptable carrier, diluent or excipient.

Furthermore, according to the present invention, there is provided a mixed vaccine which comprises effective immunogenic amounts of the abovementioned pertussis toxoid, said pertussis toxoid being adsorbed on an adjuvant, and at least one toxoid other than said pertussis toxoid, said at least one toxoid being adsorbed on an adjuvant; at least one pharmaceutically acceptable carrier, diluent or excipient; and an stabilizing agent.

Furthermore, according to the present invention, there is provided a method for producing a pertussis vaccine containing an effective immunogenic amount of a pertussis toxoid, which comprises:
(1) culturing *Bordetella pertussis* in a nutrient medium containing at least one substance selected from the group consisting of cellulose and cellulose derivatives to obtain a culture of *Bordetella pertussis,*
(2) separating said culture into a supernatant and cells of *Bordetella pertussis* and subjecting said supernatant to purification to obtain a mixed antigen comprising pertussis toxin and pertussis filamentous hemagglutinin,
(3) detoxifying said mixed antigen to obtain a pertussis toxoid,
(4) adsorbing said pertussis toxoid on an adjuvant, and
(5) adding to the resulting toxoid adsorbed on a adjuvant at least one pharmaceutically acceptable carrier, diluent or excipient and a stabilizing agent.

Furthermore, according to the present invention, there is provided a method for producing a mixed vaccine containing effective immunogenic amounts of a pertussis toxoid and at least one antigen other than said pertussis toxoid, which comprises:

(1) culturing Bordetella pertussis in a nutrient medium containing at least one substance selected from the group consisting of cellulose and cellulose derivatives to obtain a culture of *Bordetella pertussis,*
(2) separating said culture into a supernatant and cells of *Bordetella pertussis* and subjecting said supernatant to purification to obtain a mixed antigen comprising pertussis toxin and pertussis filamentous hemagglutinin,
(3) detoxifying said mixed antigen to obtain a pertussis toxoid,
(4) adsorbing said pertussis toxoid on an adjuvant,
(5) adding to the resulting pertussis toxoid at least one antigen other than said pertussis toxoid, which is adsorbed on an adjuvant, to obtain a mixture of said pertussis toxoid and said at least one antigen, and
(6) adding to said mixture at least one pharmaceutically acceptable carrier, diluent or excipient and a stabilizing agent.

Hereinbelow, the present invention will be explained in detail.

[1] Culturing of *Bordetella pertussis:*

According to the method of the present invention, *Bordetella pertussis* is cultured in a nutrient medium containing at least one substance selected from the group consisting of cellulose and cellulose derivatives.

As a nutrient medium, there may be employed conventionally known basal media for culturing *Bordetella pertussis.* As such basal media, there may be mentioned, for example, Bordet-Gengou medium, Cohen-Wheeler medium, Stainer-Scholte medium and the like [Advances in Applied Microbiology, Vol. 20, pp.27–42 (1976)]. The nutrient medium to be used in the present invention may generally be in a liquid form. Alternatively, it may also be in a solid form. The nutrient medium to be used in the present invention contains at least one substance selected from the group consisting of cellulose and cellulose derivatives. The concentration of the substance in a nutrient medium is in the range of from about 0.01 to about 2.0 w/w %.

As the cellulose derivatives, there may be employed, for example, inorganic acid esters of cellulose, organic acid esters of cellulose and ethers of cellulose. Representative examples of cellulose derivatives include acetylcellulose, cellulose xanthogenate, cellulose propionate, cellulose formate, cellulose butylate, cellulose sulfate, cellulose phosphate, cellulose acetate butyrate, methyl cellulose, ethyl cellulose, benzyl cellulose, trityl cellulose, cyanoethyl cellulose, carboxymethyl cellulose, carboxyethyl cellulose, aminoethylcellulose, oxyethylcellulose, hydroxyethyl cellulose, hydroxypropyl cellulose, hydroxypropylmethyl cellulose and acetylsuccinyl hydroxypropyl-methyl cellulose and the like. In addition, as the cellulose derivatives, there may also be employed, for example, esters of cellulose with a higher fatty acid, esters of cellulose with an unsaturated fatty acid, esters of cellulose with a dibasic fatty acid, esters of cellulose with a halogenated fatty acid, esters of cellulose with sulfonic acid, esters of cellulose with an aromatic carboxylic acid, esters of cellulose with carbamic acid, crosslinked ethers of cellulose and cationic ethers of cellulose as far as they do not have a toxicity.

The culturing is carried out statically in the case where the nutrient medium is solid. On the other hand, in the case where the nutrient medium is liquid, the culturing may be carried out statically and, alternatively, may also be carried out while stirring using a rotary shaker, a fermentation tank equipped with a stirrer, etc. Generally, the culturing may be conducted at about 30° to about 37° C. for about 20 to about 80 hours. Thus, there is obtained a culture of *Bordetella pertussis* which contains a mixed antigen comprising pertussis toxin (PT) and filamentous hemagglutinin (F-HA) in a large amount.

[2] Recovery and purification of a mixed antigen comprising PT and F-HA:

A mixed antigen comprising PT and F-HA is obtained from the culture mentioned above by separating the culture into a supernatant and cells of *Bordetella pertussis* and subjecting the supernatant to purification. The separation of the culture into a supernatant and cells may be carried out by a well-known customary technique such as low-rotating speed centrifugation and high-rotating speed centrifugation. Then, the thus obtained supernatant is subjected to purification. In carrying out the purification, conventional techniques may be used in combination. As such conventional techniques, there may be mentioned, for example, low-rotating speed centrifugation, high-rotating speed centrifugation, ultracentrifugation, salting out, precipitation by means of an organic solvent etc., adsorption treatment with an adsorbent such as charcoal powders and various gels, dialysis, filtration, ultrafiltration and the like. As described above, in purifying the mixed antigen of the present invention, there are not required any complicated, troublesome and expensive techniques such as electrophoresis and affinity column chromatography. Therefore, the mixed antigen can be obtained efficiently at low cost as compared with the conventional methods. The thus obtained antigen contains PT and F-HA in a weight ratio of about 1:1. The weight of each of PT and F-HA contained in the mixed antigen may be determined according to the method as described later in Referential Example 9.

The mixed antigen is useful not only as a raw material for producing a pertussis vaccine but also as a diagnostic for pertussis.

[3] Preparation of a pertussis toxoid:

The mixed antigen obtained above is detoxified according to a customary technique. For example, the detoxification of the antigen may be carried out as follows. That is, to the mixed antigen containing PT and F-HA is added an inactivating agent such as formalin, and sufficiently mixed to detoxify the antigen. Then, the resulting mixture is subjected to dialysis to remove the inactivating agent. From the resulting dialysate, the pertussis toxoid may be obtained by a customary method such as lyophilization, precipitation using an organic solvent etc.

[4] Preparation of an original pertussis vaccine solution:

The above-obtained dialysate containing the pertussis toxoid is diluted with a phosphate buffer etc. so that the pertussis toxoid concentration in the resulting mixture becomes about 40 to about 60 $\mu$g-protein nitrogen per ml. The thus obtained solution is used as an original pertussis vaccine solution.

[5] Preparation of an adsorbed pertussis vaccine:

The original pertussis vaccine solution obtained above is diluted with a buffer such as a phosphate buffer, and to the resulting dilution is added an adjuvant, thereby to adsorb the pertussis toxoid on the adjuvant. For example, the original pertussis vaccine solution may be diluted with a 1/75M phosphate buffer, and to the resulting mixture may be added aluminum hydroxide gel as an adjuvant so that the concentration of the added gel becomes about 0.1 to 0.8 mg/ml. As an adjuvant, there may also be employed precipitating depositary adjuvants such as calcium phosphate gel, aluminum phosphate gel, aluminum sulfate, alumina and bentonite, and antigen-production inducing adjuvants such as muramyl peptide derivatives, polynucleotides, Krestin and picibanil. From the mixture, the gel adsorbing the pertussis toxoid is obtained by, for example, centrifugation, etc. and to the resulting gel is added at least one pharmaceutically acceptable carrier, excipient or diluent, for example, a buffer such as a phosphate buffer. Then, the thus obtained pertussis vaccine solution containing a gel-adsorbed pertussis toxoid is separately poured into a small vessel such as an ampul and vial and sealed. Thus, there is obtained a purified adsorbed pertussis vaccine comprising an adsorbed pertussis toxoid in an effective immunogenic amount for giving a phylactic ability to a person who receives the inoculation of the vaccine. Such an effective immunogenic amount of the pertussis toxoid in the vaccine may be in the range of from about 7 to about 15 $\mu$g-protein nitrogen per ml. It is not preferable to use the pertussis toxoid in an amount of more than about 15 $\mu$g-protein nitrogen per ml, because any appreciable increase in immunization effect is not obtained but the cost for the preparation of a vaccine increass. Also, it is not preferable to use the pertussis vaccine in an amount of less than about 7 $\mu$g-protein nitrogen per ml, because the desired immunization effect is not always exerted. Incidentally, the quality of the vaccine produced is examined in accordance with "Adsorbed Pertussis Vaccine" provided for in Notification No. 159 of the Ministry of Health and Welfare, Japan, "Minimum Requirements for Biological Products". The thus produced adsorbed pertussis vaccine is liquid. The adsorbed pertussis vaccine may be subjected to lyophilization to obtain an adsorbed pertussis vaccine in a dried form. Such a dried adsorbed pertussis vaccine has improved heat resistance and cold resistance. The lyophilization may generally be conducted according to a customary method after the liquid adsorbed pertussis vaccine is put in a vessel such as a vial and ampul. After lyophilization, a nitrogen gas is introduced in the vessel containing the dried vaccine, followed by sealing. Then, the dried vaccine is stored. From the standpoint of stability during the storage, it is preferable that the adsorbed pertussis vaccine be in a dried form.

Further, according to the present invention, in order to increase the stability of the pertussis toxoid in the vaccine, a stabilizing agent may be added to the adsorbed pertussis vaccine which in a liquid form. As a stabilizing agent which may be used in the present invention, there may be mentioned a gelatin and gelatin derivatives. The gelatin and gelatin derivatives may be used alone or in combination. As the gelatin, there may be used, for example, a purified gelatin as described in Japanese Pharmacopoeia and the like. As the gelatin derivatives, there may be used, for example, Gelysate ® (manufactured and sold by BBL Co., Ltd., U.S.A.), Physiogewl ®, Neoplasmagel ®, Gelifundol ®, Haemaccel ® (manufactured and sold by Hoechst AG, West Germany) (which is also called Polygeline), etc. The details of the above-mentioned gelatin derivatives are described in Developments in Biological Standardization, published by S. Karger, 48, 207-234 (1981). Of them, the Haemaccel may most preferably be employed because the safeness of the Haemaccel is confirmed and the Haemaccel is used as a blood substitute or plasma substitute for human bodies. The above-mentioned stabilizing agent may be added to a liquid adsorbed pertussis vaccine in such an amount that the concentration of the stabilizing agent in the resulting mixture may become about 0.1 to about 5.0% by weight.

When two or more different kinds of stabilizing agents are employed, they are added in such an amount that the total amount thereof falls within the amount range as mentioned above.

Further, in addition to the above-mentioned stabilizing agent, according to need, there may be added to the liquid pertussis vaccine at least one of the customary known stabilizing agents, for example, saccharides such as glucose, fructose, galactose, sucrose and lactose, and amino acids such as glycine, alanine, lysine, arginine and glutamine. Such a stabilizing agent may be added in such an amount that the concentration of each stabilizing agent in the resulting mixture may become about 0.1 to about 8.0% by weight.

The thus produced pertussis vaccine containing a stabilizing agent is in a liquid form. The liquid pertussis vaccine may be lyophilized in a manner as mentioned above to obtain an adsorbed pertussis vaccine in a dried form which contains a stabilizing agent. From the standpoint of stability during the storage, it is preferable that the adsorbed pertussis vaccine containing a stabilizing agent be in a dried form.

The quality of the above-mentioned adsorbed pertussis vaccine either in a liquid form or in a dried form may be examined in accordance with the above-mentioned Notification No. 159 issued by the Ministry of Health and Welfare, Japan.

[6] Preparation of a mixed vaccine:

The vaccine of the present invention may be prepared in the form of a mixed vaccine which contains an adsorbed pertussis toxoid according to the present invention and at least one antigen other than the present pertussis toxoid. As the antigen other than the present pertussis toxoid, there may be employed any antigens that are conventionally used as active ingredients of the corresponding vaccines insofar as the side effects and adverse reactions caused by such other antigens and the pertussis toxoid are not additively or synergistically increased by the use of the pertussis toxoid and such other antigens in combination and the antigenicities and immunogenicities of the pertussis toxoid and such other antigens are not reduced by the interference between the pertussis toxoid and other antigens. The number and the kind of the antigens which may be mixed with the pertussis toxoid is not limited insofar as the side effects and adverse reactions are not increased additively or synergistically and the antigenicity and immunogenicity of each of the pertussis toxoid and such antigens are not reduced as mentioned above. Generally, two to six kinds of antigens other than the pertussis toxoid may be mixed with the pertussis toxoid. As the antigens which may be mixed with the present pertussis toxoid, there may be mentioned, for example, detoxified antigens, inactivated antigens or toxoids which are derived from diphtheria bacillus, tetanus bacillus, typhoid bacillus, paratyphoid bacillus, cholera bacillus, gonococcus, meningococcus, *Pseudomonas aeruginosa, Escherichia coli, Haemophilus influenza,* Streptococcus group A and group B, *Streptococcus pneumoniae,* pneumococcus, *Legionella, Rickettsia prowazekii, Rickettsia reckettsii,* leptospira, *Leptospira interohaemorrhagia* (the pathogen of Weil's disease), malarial parasites, *Coccidioides immitis,* blood fluke, toxoplasma, trypanosoma, leishmania, hepatitis B virus, Japanese encephalitis virus, influenza viruses types A and B, parainfluenza virus, AIDS virus, venoms of the snakes belonging to Trimeresurus and the like. Further, customary known artificial antigens may also be employed. The above-mentioned antigens may be adsorbed on an adjuvant. As an adjuvant, there may be employed those mentioned before.

The mixed vaccine of the present invention may be prepared as follows. The original pertussis vaccine solution containing a pertussis toxoid is obtained as described in item [4] mentioned before. Separately, solutions each containing an antigen which is to be mixed with the pertussis toxoid are prepared according to a customary method. Then, to the original pertussis vaccine solution containing the pertussis toxoid are added the solution or solutions each containing an antigen other than the pertussis toxoid. Then, to the resulting mixture is added at least one pharmaceutically acceptable carrier, diluent or excipient. The mixed vaccine of the present invention is prepared so that the mixed vaccine may contain the pertussis toxoid in an effective immunogenic amount, namely, in an amount of about 7 to 15 μg-protein antigen per ml of the mixed vaccine, and an effective immunogenic amount of each antigen other than pertussis toxoid. The effective immunogenic amount of each antigen other than pertussis toxoid varies according to the kind of the antigen.

As an illustrative example of the preparation of a mixed vaccine of the present invention, the preparation of a mixed vaccine comprising the pertussis toxoid, diphtheria toxoid and tetanus toxoid will be explained below. From the culture of diphtheria bacillus obtained by a customary method, a diphtheria toxoid is isolated and purified by a customary known method. In substantially the same manner as described in item [3] mentioned before, the purified diphteria toxoid is detoxified and an original diphteria vaccine solution is prepared in substantially the same manner as in item [4] as mentioned before. Separately, an original tetanus vaccine solution is prepared from the culture of tetanus bacillus in substantially the same manner as mentioned just above. With respect to the pertussis toxoid, the original pertussis vaccine solution obtained in item [3] mentioned above is used. To each of the thus obtained original vaccine solutions is added an adjuvant, thereby to obtain original adsorbed vaccine solutions. The thus obtained adsorbed vaccine solutions are mixed in ratios such that the concentrations of the pertussis toxoid, diphteria toxoid and tetanus toxoid may become about 21 to about 45 μg-protein nitrogen per ml, about 90 Lf/ml and about 21 Lf/ml, respectively. Thus, there is obtained a mixed vaccine containing an adsorbed pertussis toxoid, adsorbed diphtheria toxoid and adsorbed tetanus toxoid. To the thus obtained mixed vaccine, at least one stabilizing agent selected from the group consisting of a gelatin and gelatin derivatives may be added in an amount such that the concentration of the stabilizing agent becomes about 0.1 to about 5.0% by weight.

The above-obtained mixed vaccine is subjected to lyophilization to obtain a dried mixed vaccine. The thus obtained dried mixed vaccine contains the above-mentioned stabilizing agent in such an amount as will, when the mixed vaccine is dissolved in water to obtain an aqueous solution containing pertussis toxoid at a concentration of about 7 to about 15 μg-protein nitrogen per ml, give a stabilizing agent concentration of about 0.1 to about 5.0% by weight. The quality of the thus produced vaccine is examined in accordance with "Mixed Adsorbed Vaccine for Pertussis, Diphtheria and Tetanus" provided for in Notification No. 159 of the Ministry of Health and Welfare, Japan, "Minimum Requirements for Biological Products". A mixed vaccine of the present invention is not limited to the above-mentioned mixed vaccine, and can be produced by mixing a pertussis toxoid of the present invention with any antigens as mentioned before.

Generally, the vaccine of the present invention may be contained and sealed in a vial, ampul or the like. The vaccine of the present invention may generally be administered in the form of a liquid or suspension. In the case where the vaccine is in a dried form, the vaccine is dissolved or suspended in sterilized distilled water before administration. The concentration of the pertussis toxoid in the vaccine of the present invention may generally be about 7 to about 15 μg-protein nitrogen per ml as mentioned before. Generally, the vaccine may be administered subcutaneously. The dose of the vaccine per person may generally be about 0.5 ml. The vaccine may generally be administered thrice at intervals of about three to eight weeks and then, about one year to one and a half year later, administered once more.

[7] Preparation of a diagnostic for pertussis:

As mentioned before, the mixed antigen of the present invention is also useful as a diagnostic for pertussis, particularly an immunological diagnostic for detecting the infections with pertussis and for determining whether or not patients suffer from pertussis. In general, for preparing a diagnostic for pertussis, the mixed antigen of the present invention is separated into components, namely, PT and F-HA, and each of the PT and F-HA is used alone as a diagnostic. The separation of the mixed antigen into PT and F-HA may generally be carried out be a customary technique such as a hydroxyapatite column chromatography. Each of the PT and F-HA can be effectively used in the diagnoses by ELISA (Enzyme-linked immunosorbent assay), reverse passive hemagglutination reaction test and other various tests in which an antigen or antibody labelled with a fluorescent pigment, enzyme, radioisotope or the like is utilized. Generally, for the use as a diagnostic, each of the PT and F-HA may be separately contained and sealed in a vial or small test tube. Alternatively, each of the PT and F-HA may also be separately adsorbed on the surface of a customary filter paper, membrane or microplate.

The present invention has the following advantages.

(1) According to the method of the present invention for culturing *Bordetella pertussis*, there can be obtained a culture which contains a mixed antigen comprising PT and F-HA in an increased amount. Further, according to the present method, such a culture can be obtained at low cost as compared with those obtained according to conventional techniques such as a technique in which *Bordetella pertussis* is cultured in the presence of cyclodextrin, because the cellulose and cellulose derivatives used in the present invention is easily available at low cost.

(2) The weight ration of PT and F-HA in the present mixed antigen, which PT and F-HA are raw materials for the active ingredients of the present vaccine, is about 1:1. This is advantageous because it is preferred that the pertussis vaccine contain toxoids derived respectively from PT and F-HA in a weight ratio of about 1:1 from the standpoint of effectiveness, and such a pertussis vaccine can be effectively and labor-savingly produced from the mixed antigen of the present invention.

(3) After culturing, the cellulose and cellulose derivatives can be easily removed from the culture and, therefore, there can be easily and efficiently obtained a high purity PT and F-HA at low cost.

(4) The thus obtained PT and F-HA are uniform in quality and, therefore, the pertussis toxoid of the present invention, which is obtained from the PT and F-HA through a customary detoxification process using formalin, is also uniform in quality. Further, the present pertussis toxoid does not revert to a toxic state during preservation. Therefore, the present toxoid is excellent in stability and safety.

(5) The titer of the dried vaccine of the present invention containing at least one substance selected from the group consisting of a gelatin and its derivatives as a stabilizing agent is not decreased during the storage for 3 years at a temperature in the range of −20° C. to 37° C. and for more than 3 months at 50° C. The present dried vaccine is extremely stable and convenient.

Hereinafter, the present invention will now be described in detail with reference to the following Referential Examples and Examples, which should not be construed to be limiting the scope of the present invention.

REFERENTIAL EXAMPLE 1

Preparation of a modified Stainer-Scholte medium

The first group of components as indicated below and the second group of components as indicated below are separately dissolved in appropriate volumes of distilled water to obtain two solutions. Then, the solution containing the first group of components is sterilized by means of an autoclave. On the other hand, the solution containing the second group of components is sterilized by means of filtration. Before use, both the sterilized solutions are mixed, and to the mixture is added sterilized water so that the total volume of the mixture becomes 10 l.

| | |
|---|---|
| First group of components: | |
| Sodium chloride | 25.0 g |
| Sodium dihydrogen phosphate | 5.0 g |
| Magnesium chloride hexahydrate | 1.0 g |
| Calcium chloride dihydrate | 0.2 g |
| Copper sulfate pentahydrate | 0.005 g |
| Casamino acid | 100.0 g |
| L-proline | 2.4 g |
| Sodium glutamate | 100.0 g |
| Tris | 15.3 g |
| Second group of components: | |
| L-cystine | 0.4 g |
| Ferrous sulfate heptahydrate | 0.1 g |
| Ascorbic acid | 0.2 g |
| Niacin | 0.4 g |

REFERENTIAL EXAMPLE 2

Preparation of an improved Pope medium

The medium comprises the following composition and is used after sterilization by means of an autoclave.

| | |
|---|---|
| Calcium chloride | 0.6 g |
| Disodium hydrogenphosphate | 1.0 g |
| L-cystine | 0.15 g |
| Maltose | 31.0 g |
| Solution II(1) | 4.0 g |
| Digested beef solution(2) | 1000.0 ml |
| Note: (1)The composition of Solution II is as follows. | |
| Magnesium sulfate | 2.25 g |
| Copper sulfate | 0.5 g |
| Manganese chloride | 0.15 g |
| Zinc sulfate | 0.4 g |
| β-alanine | 1.15 g |
| Nicotinic acid | 1.15 g |
| Pimelic acid | 0.075 g |
| Hydrochloric acid | 30.0 ml |
| Distilled water | 1000.0 ml |

(2)A digested beef solution is prepared as follows.
To 17 l of distilled water is added 5.1 kg of minced beef. The resulting mixture is allowed to stand overnight. Then, the temperature of the thus obtained mixture is raised and maintained at 60° C. on a water bath, and to the mixture is added 6.2 g of a papain [manufactured by Merck & Co., Inc., U.S.A. (egg-white hydrolizing ability 1:350)] and the mixture is stirred for 2 hours to digest the minced beef in the mixture. Then, the resulting mixture is heated at 90 to 95° C. for 10 minutes. Thereafter, to the mixture is added Celite as a filter aid, and the obtained mixture is subjected to filtration using a filter paper. The thus obtained -continued filtrate is used as a digested beef solution.

REFERENTIAL EXAMPLE 3

Preparation of an improved PII medium The medium comprises the following composition and is used after sterilization by means of an autoclave.

| | |
|---|---|
| Heart extract[1] | 15.0 g |
| Polypeptone[2] | 20.0 g |
| Sodium chloride | 5.0 g |
| Magnesium sulfate | 0.2 g |
| Disodium hydrogenphosphate | 0.16 g |
| Pottasium dihydrogenphosphate | 0.1 g |
| Glucose | 7.5 g |
| Reduced iron | 0.25 g |
| Distilled water | 1000.0 ml |

Note:
[1] Heart extract is manufactured and sold by Nissui Pharmaceutical Co., Ltd., Japan.
[2] Polypeptone is manufactured and sold by Daigo Eiyo Kagaku Co., Ltd., Japan.

REFERENTIAL EXAMPLE 4

Preparation of a phosphate buffer

A phosphate buffer is prepared by mixing an aqueous disodium hydrogenphosphate solution having a desired concentration with an aqueous pottasium dihydrogenphosphate solution having the same concentration as that of the disodium hydrogenphosphate solution in such a volume ratio that the resulting mixture has a desired pH.

REFERENTIAL EXAMPLE 5

Preparation of a phosphate-buffered saline (PBS)

PBS is prepared by dissolving disodium hydrogenphosphate and pottasium dihydrogenphosphate in a solution containing 6.8 g/l of sodium chloride so that the resulting solution has a desired pH.

REFERENTIAL EXAMPLE 6

Determination of the cell concentration of bacteria

The cell concentration of bacteria in a medium is determined by turbidimetry. Using a colorimeter model Junior II (manufactured and sold by Coleman Co., Ltd., U.S.A.) The cell concentration of bacteria in a culture is determined based on the turbidity of the culture by the comparison with the turbidity of a standard bacterium solution having a known cell concentration (available from the National Institute of Health, Japan). The cell concentration in the culture is indicated by IOU/ml (IOU: International Opacity Unit).

REFERENTIAL EXAMPLE 7

The assay of F-HA titer

From a 3-days old chicken, erythrocytes are obtained. The erythrocytes are fixed with formalin and the formalin-fixed erythrocytes are suspended in a 1/75M PBS containing 0.1 w/v % bovine serum albumin, 0.001 w/v % gelatin and 0.1 w/v % sodium nitride at an erythrocyte concentration of 0.6 v/v %. A sample of which the F-HA titer is to be determined is subjected to doubling dilution. To each of the resulting dilutions is added an equi-volume of the above-mentioned erythrocyte suspension, followed by stirring. Then, each of the resulting mixtures is observed with naked eyes as to whether or not complete hemagglutination is caused in the mixture. From the results of the observation, the highest dilution ratio at which complete hemagglutination is still caused is obtained. F-HA titer of the sample is defined as a reciprocal of the thus obtained highest dilution ratio and indicated as HAU. Incidentally, for diluting the sample, 1/75M PBS containing 0.2 w/v % bovine serum albumin is used.

REFERENTIAL EXAMPLE 8

The assay of PT titer

A human haptoglobin (manufactured and sold by Green Cross Corporation, Japan) is dissolved in a sodium carbonate buffer (pH 9.6) so that the final concentration of the human haptoglobin becomes 2 $\mu$g/ml. The thus obtained mixture is allowed to stand at 4° C. overnight on a polystyrene-made microplate (manufactured and sold by Greiner Co., Ltd., West Germany) so that the haptoglobin is adsorbed and immobilized on the microplate. Using the thus obtained haptoglobin-immobilized microplate together with an anti-PT rabbit serum and alkaline phosphatase-linked anti-rabbit IgG, the PT titer of the sample is assayed by a customary known ELISA method. The result of the assay is automatically read by an autoreader for ELISA (manufactured and sold by Dinatech Co., Ltd., U.S.A.) and calculated by an electronic computer to obtain a PT titer. The PT titer is indicated by ELISA U/ml.

Incidentally, the anti-PT rabbit serum is obtained as follows. A PT is adsorbed on aluminum phosphate and injected to a rabbit subcutaneously. About 40 days later, the blood is obtained from the rabbit and subjected to centrifugation. Thus, the anti-PT rabbit serum is obtained. The alkaline phosphatase-linked anti-rabbit IgG is manufactured and sold by Miles-Yeda Co., Ltd., Israel.

REFERENTIAL EXAMPLE 9

Determination of the weight ratio of F-HA and PT

Method (A): Using the standard samples of F-HA and PT having known activities and protein quantities and a purity of about 100% (which are available from the National Institute of Health, Japan), the respective activities of the F-HA and PT of a sample are assayed by a customary known ELISA method, and based on the thus obtained activities, the weight ratio of the F-HA and PT is calculated.

Method (B): Under an acidic condition, a sample is subjected to polyacrylamide gel electrophoresis. Then, the thus obtained gel is stained with Coomassie Briliant Blue to visualize the bands of the PT and F-HA. Then, the gel is subjected to densitometry to measure the areas of the bands. From the area of each band of the F-HA and PT, the weight ratio of the F-HA and PT is calculated.

Based on both the calculated weight ratios obtained by the above-mentioned methods (A) and (B), the weight ratio of F-HA and PT is finally determined.

REFERENTIAL EXAMPLE 10

Determination of the amount of an endotoxin

The amount of an endotoxin in a sample is determined using a Limulus test kit Wako (manufactured and sold by Wako Pure Chemical Industries Ltd., Japan). In the Limulus test, a Limulus amebocyte lysate (LAL) is used.

REFERENTIAL EXAMPLE 11

Negative test of reversion of a toxoid to a toxin

The test is carried out in accordance with the the mouse leukocytes-increasing test and histamine sensitization test defined in "Pertussis vaccine" provided in Notification No.159 of the Ministry of Health and Welfare, Japan, "Minimum Requirements for Biological Products".

REFERENTIAL EXAMPLE 12

Assay for determination of the titers of both diphtheria toxoid and tetanus toxoid According to a customary flocculation test by the use of a standard anti-toxin (available from the National Institute of Health, Japan), both the titers of diphtheria toxoid and tetanus toxoid are assayed. The titers are indicated as Lf/ml.

REFERENTIAL EXAMPLE 13

Determination of the toxoid titer of a vaccine in vivo (A) With respect to a pertussis toxoid, the titer is assayed by a mouse intracerebral challenge method.

(B) With respect to a diphtheria toxoid, the titer is assayed by a rabbit intracutaneous injection method.

(C) With respect to a tetanus toxoid, the titer is assayed by a toxin challenge method on immunized ginea pigs and immunized mice.

With respect to the above-mentioned assays, reference may be made to "Purified adsorbed pertussis vaccine", "Adsorbed diphtheria toxoid" and "Adsorbed tetanus toxoid" provided for in Notification No.159 of the Ministry of Health and Welfare, Japan, "Minimum Requirements for Biological Products". The titers obtained by the above-mentioned assays are expressed in terms of IU/ml (IU: International Unit).

REFERENTIAL EXAMPLE 14

Determination of the amount of protein nitrogen

To a sample is added trichloroacetic acid to precipitate a protein. The thus precipitated protein is collected and subjected to determination of the amount of protein nitrogen by a customary known micro-Kjeldahl method.

EXAMPLE 1

[Cultivation of Bordetella pertussis strain TOHAMA (phase I)]

141 l of a solution containing the above-mentioned first group of components for a modified Stainer-Sholte medium in an amount necessary for preparing 150 l of the medium is prepared according to the description of Referential Example 1. Then, the solution is put in a fermentation tank which has a capacity of 200 l and is equipped with a stirring blade and, at its bottom, a sparger for introducing air into the tank. Then, the solution in the tank is sterilized at 120° C. for 30 min under pressure, followed by cooling. To the sterilized solution are added a 1500 ml of sterilized solution containing the above-mentioned second group of components for a modified Stainer-Sholte medium in an amount necessary for preparing 150 l of the medium, and 7500 ml of a sterilized 2 w/w % methyl cellulose solution and mixed, thereby to prepare a liquid medium which contains methyl cellulose at a concentration of 0.10% by weight. Then, to the thus prepared medium is inoculated Bordetella pertussis strain TOHAMA (phase I) so that the final cell concentration of the strain becomes 0.5 IOU/ml. The strain TOHAMA (phase I) is maintained at the National Institute of Health, Japan and available from the institute. Also, this strain is deposited at the Institute for Fermentation, Osaka, Japan under the accession number IFO-14073. Then, the resulting medium is cultured at 35° C. for 48 hours while stirring and aerating. The stirring of the medium is conducted by rotating the stirring blade at 220 rpm and the aeration of the medium is conducted by introducing air at a flow rate of 50 l/min through a sparger provided at the bottom of the fermentation tank.

Separately, substantially the same procedures as described above are repeated except that the concentration of methyl cellulose in the medium is varied as indicated in Table 1.

24 hours and 48 hours after the initiation of the incubation, 50 ml samples are taken from the culture. The samples are subjected to determination of the cell concentration of the strain and determination of the F-HA titer and PT titer in accordance with the methods described in Referential Examples 6, 7 and 8. The results are shown in Table 1. As is apparent from Table 1, the addition of methyl cellulose remarkably increases the yields of the F-HA and PT. That is, the yields of the F-HA and PT are about 10 to 100 times those of the F-HA and PT in the case where no methyl cellulose is added to a medium. Further, the weight ratio of the F-HA to the PT is found to be about 1:1.

TABLE 1

| Concentration of methyl cellulose added (w/w %) | Time after initiation of incubation (hours) | Cell concentration (IOU/ml) | F-HA titer (HAU) | PT titer (ELISA U/ml) |
|---|---|---|---|---|
| None | 24 | 37 | 4 | 110 |
|  | 48 | 115 | 2 | 160 |
| 0.02 | 24 | 50 | 16 | 550 |
|  | 48 | 128 | 512 | 1800 |
| 0.10 | 24 | 48 | 64 | 740 |
|  | 48 | 130 | 2048 | 2550 |
| 0.50 | 24 | 53 | 64 | 710 |
|  | 48 | 140 | 2048 | 2100 |

EXAMPLE 2

(Purification of F-HA and PT)

Using a continuous flow centrifuge, the culture of Bordetella pertussis obtained in Example 1 is subjected to centrifugation at 13,500 rpm at a flow rate of 800 ml/min to obtain a supernatant. Then, to 10 l of the supernatant is added 4 kg of ammonium sulfate to conduct salting out, thereby to form precipitates therein. The precipitates-formed mixture is subjected to centrifugation to separate the mixture into the precipitates and a supernatant, and the precipitates are collected. The collected precipitates are dissolved in 0.05 M phosphate buffer containing 1 M sodium chloride and the thus obtained mixture is applied to a sucrose solution having a sucrose density gradient of from 5 to 15 w/w % put in a centrifuge tube, followed by centrifugation at 33,000 rpm for 20 hours using a zonal centrifuge. After the centrifugation, the solution obtained by the above-mentioned centrifugation is divided into 30 fractions in the order of their respective sucrose concentrations from low to high. Of the 30 fractions, the 14th to 22nd fractions are collected as a fraction containing a purified pertussis antigen and employed in the subsequent procedures. Incidentally, the F-HA titer, PT titer and endotoxin titer of the purified pertussis antigen are assayed according to the methods described in Referential Examples 8, 9 and 10. As a result, it is found that regarding each titer of F-HA, PT and endotoxin contained in the culture obtained in Example 1 as 100%, the recoveries of F-HA and PT after the zonal centrifugation are 60% and 57%, respectively, while the percentage of the endotoxin remaining unremoved is 0.001% (99.999% of the endotoxin is removed).

EXAMPLE 3

[Preparation of an original pertussis toxoid (hereinafter often referred to as "P")]

The purified pertussis antigen fraction obtained in Example 2 is diluted with 1/20 M phosphate buffer to obtain a diluted solution containing 50.0 µg/ml of a protein-nitrogen derived from the above-mentioned fraction. Then, to the diluted solution is added formalin and L-lysine so that the final concentrations of formalin and L-lysine become 0.4 v/v % and 0.05 mole, respectively. The obtained mixture was stirred, followed by heat-treatment at 35° C. for 20 days, thereby to detoxify the antigens, namely F-HA and PT, contained therein. The thus obtained mixture is dialyzed at 4° C. for 24 hours against 1/20 M phosphate buffer, thereby to eliminate the formalin and L-lysine. The resulting dialysate is used as an original pertussis toxoid (P) solution.

EXAMPLE 4

(Preparation of liquid adsorbed pertussis vaccine)

The original P solution obtained in Example 3 is diluted with 1/40 M phosphate buffer (pH 6.0) so that the concentration of protein nitrogen becomes 10 µg/ml. To the resulting solution is added aluminum phosphate gel in such an amount that the the aluminum phosphate gel concentration becomes 0.2 mg Al/ml. The resulting mixture is stirred at 4° C. for 5 hours to allow the pertussis toxoid to be adsorbed on the gel. Subsequently, the mixture is subjected to centrifugation using a centrifuge (manufactured and sold by Kokusan Enshinki Co., Ltd., Japan) at 2,000 rpm at 4° C. for 20 min to form a gel layer and the gel layer is collected. The collected gel is suspended in 1/75 M phosphate buffer (pH 6.5) so that the final concentrations of the pertussis toxoid and aluminum phosphate gel become 10 µg-protein nitrogen/ml and 0.2 mg-Al/ml, respectively. Then, to the resulting suspension are added sucrose, L-arginine and Haemaccel (manufactured and sold by Hoechst Co., Ltd., West Germany) in this order so that the final concentrations thereof become 3 w/v %, 1 w/v % and 2 w/v %, respectively. Then, the obtained mixture is put in 10 ml-vials in an amount of 10 ml per vial to obtain a liquid adsorbed pertussis toxoid.

Substantially the same procedures as mentioned above are repeated except that the concentration of Haemaccel is varied.

Some of the vials thus prepared are used for preservation test which will be described later in Application Example 1.

It is confirmed that the thus obtained pertussis toxoid passes various tests in accordance with the provision "Purified adsorbed pertussis toxoid" provided for in the Notification No.159 of Japanese Ministry of Health and Welfare, "Minimum Requirements for Biological Products".

EXAMPLE 5

(Preparation of a dried adsorbed pertussis vaccine)

Substantially the same procedures as in Example 4 are repeated to obtain a gel to which the pertussis toxoid is adsorbed. The resulting gel is suspended in 1/75M phosphate buffer (pH 6.5) in a ratio such that the final volume of the resulting suspension becomes one fifth that of the pertussis toxoid solution before the toxoid is adsorbed on the gel, and to the resulting suspension are added sucrose, L-arginine and Haemaccel in this order in such amounts that when water is added to the resulting suspension to obtain a 10 ml suspension, the concentrations of sucrose, L-arginine and Haemaccel in the suspension will become 3 w/v %, 1 w/v % and 2 w/v %, respectively. The thus obtained suspension is put in 10 ml-vials in an amount of 2.0 ml per vial. Some of the thus obtained vials are used for preservation test which will be described later in Application Example 1, and the rest of the vials are subjected to lyophilization to obtain a dried adsorbed pertussis vaccine. The lyophilization is conducted as follows. The adsorbed pertussis toxoid suspension in the vials are frozen at −43° C. for 3 hours. Then, the frozen suspension is subjected to lyophilization under a pressure of 2 to $4\times10^{-2}$ millibar successively at −30° C. for 53 hours and 30° C. for 8 hours using a lyophilizer model L-80V manufactured and sold by Edwards Co., Italy.

Substantially the same procedures as mentioned above are repeated except that the concentration of Haemaccel added is varied, thereby to obtain a dried adsorbed pertussis vaccine.

The thus obtained dried adsorbed pertussis vaccine in each vial is suspended in sterilized distilled water so that the final volume becomes 10 ml. It is confirmed that this toxoid suspension passes various tests in accordance with the provision "Purified Adsorbed Pertussis Toxoid" provided for in the Notification No.159 of Japanese Ministry of Health and Welfare, "Minimum Requirements for Biological Products".

REFERENTIAL EXAMPLE 15

[Preparation of diphtheria toxoid (hereinafter often referred to as "D")]

Diphtheria bacillus Park-Williams strain (ATCC 13812) is inoculated into 150 l of an improved Pope medium described in Referential Example 2 put in a fermentation tank having a capacity of 200 l as used in Example 1 and cultured while aerating with an areration rate of 700 ml/min and stirring by the rotation of a stirring blade at 200 rpm at 35° C. for 48 hours. After the incubation, the resulting culture is subjected to continuous flow centrifugation using a centrifuge model CSA8 (manufactured and sold by Westfalia Co., U.S.A.) at room temperature at 9160 rpm and a flow rate of 3 l/min to obtain a supernatant. To 1 l of the supernatant is added 3 g of Celite as a filter aid, followed by filtration using a filter paper to obtain a filtrate. Subsequently, the filtrate is condensed using a ultrafiltration membrane (Module SIP 3013 manufactured and sold by Asahi Chemical Co., Ltd., Japan; cut-off molecular weight : 6000) to make the volume of the filtrate one twentieth. The resulting filtrate is subjected to purification. The purification is effected as follows. To the condensed filtrate is added 0.5 w/v % of activated carbon powder, and subjected to centrifugation to obtain a supernatant. To the supernatant is added a saturated aqueous ammonium sulfate solution in a supernatant-to-ammonium sulfate solution volume ratio of 40:60 to effect salting-out, thereby forming precipitates. The precipitates are collected and dissolved in 0.02M phosphate buffer (pH 7.0), followed by dialysis against 0.02M phosphate buffer (pH 7.0) overnight. The thus obtained dialysate is applied to a DEAE column. Then, using 0.04M phosphate buffer (pH 7.0) as an eluent, elution of the DEAE column is carried out to obtain a purified D solution as an eluate. After the purification, the purified product is detoxified in substantially the same manner as in Example 3 to obtain an original D solution.

REFERENTIAL EXAMPLE 16

[Preparation of tetanus toxoid (hereinafter referred to as "T")]

Into 150 l of an improved PII medium described in Referential Example 3 put in a fermentation tank as used in Step 1 is inoculated tetanus bacillus Harvard strain (ATCC 10779), followed by culturing under an anaerobic condition at 35° C. for 4 days while introducing nitrogen gas into the tank at a flow rate of 5 l/min through a sparger at the bottom of the fermentation tank. To 1 l of the resulting culture is added 3 g of Celite as a filter aid, followed by mixing and subjected to filtration using a filter paper. To the thus obtained filtrate is added, while stirring, formalin so that the final concentration of the formalin becomes 0.4 v/v %. The resulting mixture is allowed to stand at 35° C. for 4 days to detoxify the tetanus toxin in the mixture. After the detoxification, the obtained solution is subjected to purification in substantially the same manner as in Referential Example 15 to obtain an original T solution.

EXAMPLE 6

[Preparation of a purified adsorbed diphtheria-pertussis-tetanus (hereinafter often referred to as "DPT") mixed vaccine]

The original P, D and T solutions obtained in Examples 3, 6 and 7 each are respectively diluted with 1/20M PBS so that the antigen content becomes 30 μg-protein nitrogen/ml with respect to P, 90 Lf/ml with respect to D and 21 Lf/ml with respect to T. Then, to each of the resulting solutions is added an aluminum phosphate gel in substantially the same manner as in Example 4 to adsorb each toxoid on the gel. Then, equi-volumes of the respective resulting solutions are mixed. Subsequently, to the mixture are added sucrose, L-arginine and Haemaccel in this order so that the final concentrations of the sucrose, L-arginine and Haemauel become 2 w/w %, 1 w/w % and 1 w/w %, respectively. The resulting DPT mixed solution is put in 10 ml-vials in an amount of 10 ml per vial. It is confirmed that this vaccine passes various tests in accordance with the provision "Purified Adsorbed Mixed Vaccine for Pertussis, Diphtheria and Tetanus" provided for in the Notification No. 159 of Japanese Ministry of Health and Welfare "Minimum Requirements for Biological Products".

EXAMPLE 7

(Preparation of purified dried adsorbed DPT mixed vaccine)

The original P, D and T solutions obtained in Example 3, 6 and 7 each are respectively diluted with 1/20M PBS so that the antigen content becomes 30 μg-protein nitrogen/ml with respect to P, 90 Lf/ml with respect to D and 21 Lf/ml with respect to T. Then, to each of the resulting toxoid solutions is added an aluminum phosphate gel in substantially the same manner as in Example 4 to adsorb each toxoid on the gel. From the resulting mixture, the gel on which each toxoid is adsorbed is obtained in substantially the same manner as in Example 4. Each of the resulting gels is suspended in 1/75M phosphate buffer (pH6.5) in a ratio such that the final volume of the resulting suspension becomes one fifth that of each toxoid solution before the toxoid is adsorbed on the gel in substantially the same manner as in Example 5. Thus, there are obtained P, D and T suspensions. Then, equi-volumes of the respective P, D and T suspensions are mixed. Subsequently, to the mixture are added sucrose, L-arginine and Haemaccel in this order in such amounts that when water is added to the resulting mixture to obtain a 10 ml suspension, the concentrations of sucrose, L-arginine and Haemaccel in the solution will become 2 w/w %, 1 w/w % and 1 w/w %, respectively. The resulting suspension is put in 10 ml-vials in an amount of 2.0 ml per vial and subjected to lyophilization in substantially the same manner as in Example 5 to obtain a purified dried adsorbed DPT mixed vaccine. It is confirmed that this vaccine passes various tests in accordance with the provision "Purified Adsorbed Mixed Vaccine for Pertussis, Diphtheria and Tetanus" provided for in the Notification No. 159 of Japanese Ministry of Health and Welfare, "Minimum Requirements for Biological Products".

APPLICATION EXAMPLE 1

(Preservation test)

Each of the vaccines produced in Examples 4, 5, 6 and 7 is subjected to preservation test at −20° C., 4° C., 25° C., 37° C. and 50 ° C. for 36 months. During this period, sampling is conducted periodically with respect to each vaccine and the titers of the samples are determined in substantially the same manner as in Referential Example 13. Further, in substantially the same manner as in Referential Example 11, the samples are examined to confirm that there is no reversion of the toxoid to a toxic state. Furthermore, the samples of the liquid adsorbed vaccines are frozen at −20° C. and thawed at room temperature. This freezing and thawing procedures are repeated 10 times. Then the samples are subjected to determination of the titer of the vaccine in substantially the same manner as in Referential Example 13. As a result, it is found that the present vaccines are extremely stable under freezing-thawing circumstances.

(A) The results of the preservation test with respect to the vaccines produced in Examples 4 and 5 are shown in Tables 2 and 3. The vaccines of the present invention which contain Haemaccel as a stabilizing agent are extremely stable and exhibit no reversion of the toxoid to a toxic state during preservation.

TABLE 2

| Form of adsorbed vaccine | Stabilizing agent (w/w %) | | | Preservation temperature (°C.) | Titer (IU/ml) Preservation period (month) | | | Reversion to a toxic state |
|---|---|---|---|---|---|---|---|---|
| | Sucrose | L-arginine | Haemaccel | | 1 | 6 | 12 | |
| Liquid[1] | — | — | — | 4 | — | — | 34.5 | None[3] |
| | 3 | 1 | — | 4 | — | — | 34.5 | None |
| | 3 | 1 | 2 | 4 | — | — | 35.0 | None |
| | — | — | — | 50 | 3.2 | <1 | <1 | None |
| | 3 | 1 | — | 50 | 8.0 | 5.4 | <1 | None |
| | 3 | 1 | 2 | 50 | 27.3 | 25.0 | 7.6 | None |
| Dried[2] | — | — | — | 4 | — | — | 34.0 | None |
| | 3 | 1 | 0 | 4 | — | — | 35.5 | None |
| | 3 | 1 | 2 | 4 | — | — | 40.8 | None |
| | 3 | 1 | 0.5 | 4 | — | — | 38.1 | None |
| | 3 | 1 | 0.1 | 4 | — | — | 35.0 | None |
| | — | — | — | 50 | 10.2 | 5.4 | <1 | None |
| | 3 | 1 | 0 | 50 | 20.3 | 10.1 | 2.5 | None |
| | 3 | 1 | 2 | 50 | 40.0 | 38.0 | 35.1 | None |
| | 3 | 1 | 0.5 | 50 | 35.8 | 35.0 | 30.0 | None |
| | 3 | 1 | 0.1 | 50 | 30.8 | 20.0 | 8.6 | None |

Note
[1] The vaccine obtained in Example 4. The titer at the start of the preservation is 41.0 IU/ml.
[2] The vaccine obtained in Example 5. The titer at the start of the preservation is 41.0 IU/ml.
[3] The toxoid is not reverted to a toxic state during preservation.

(B) The adsorbed mixed vaccines containing pertussis toxoid, diphtheria toxoid and tetanus toxoid as obtained in Examples 6 and 7 are assayed for the titer of each toxoid according to the method described in Referential Example 13. The results are shown in Table 4. The vaccines obtained in Examples 6 and 7 each containing Haemaccel as a stabilizing agent are extremely stable, and the toxoid is not reverted to a toxic state during the preservation.

TABLE 3

| Form of adsorbed vaccine | Stabilizing agent (w/w %) | | | Preservation temperature (°C.) | Titer (IU/ml) Preservation period (month) | | | | Reversion to a toxic state |
|---|---|---|---|---|---|---|---|---|---|
| | Sucrose | L-arginine | Haemaccel | | 0 | 12 | 24 | 36 | |
| Liquid[1] | — | — | — | −20 | 26.8 | 18.8 | 14.1 | 10.3 | None |
| | — | — | — | 4 | " | 24.5 | 21.0 | 15.4 | None |
| | — | — | — | 25 | " | 24.2 | 20.0 | 13.2 | None |
| | — | — | — | 37 | " | 5.2 | 2.3 | <1 | None |
| Liquid[1] | 3 | 1 | 1 | −20 | 26.7 | 23.5 | 22.0 | 22.1 | None |
| | 3 | 1 | 1 | 4 | " | 24.1 | 22.8 | 21.5 | None |
| | 3 | 1 | 1 | 25 | " | 22.7 | 20.4 | 20.8 | None |
| | 3 | 1 | 1 | 37 | " | 10.2 | 6.8 | 5.4 | None |
| Dried[2] | — | — | — | −20 | 26.0 | 19.1 | 18.2 | 17.8 | None |
| | — | — | — | 4 | " | 18.7 | 17.5 | 17.4 | None |
| | — | — | — | 25 | " | 15.7 | 12.2 | 10.8 | None |
| | — | — | — | 37 | " | 14.2 | 8.6 | 6.3 | None |
| Dried[2] | 3 | 1 | 1 | −20 | 26.2 | 25.1 | 24.2 | 24.3 | None |
| | 3 | 1 | 1 | 4 | " | 26.0 | 24.4 | 25.0 | None |
| | 3 | 1 | 1 | 25 | " | 25.4 | 24.0 | 23.7 | None |
| | 3 | 1 | 1 | 37 | " | 24.8 | 24.0 | 23.5 | None |

Note
[1] The vaccine obtained in Example 4.
[2] The vaccine obtained in Example 5.

TABLE 4

| Form of adsorbed vaccine | Toxoid | Preservation temperature (°C.) | Titer (IU/ml) Preservation period (month) | | | | |
|---|---|---|---|---|---|---|---|
| | | | 0 | 6 | 12 | 24 | 36 |
| Liquid[1] | Pertussis toxoid | 4° C. | 13.5 | 13.1 | 12.0 | 11.2 | 11.1 |
| | | 25° C. | " | 12.8 | 11.0 | 10.6 | 10.3 |
| | | 37° C. | " | 12.5 | 8.0 | 4.2 | <1 |
| | Diphtheria toxoid | 4° C. | 120 | 122 | 115 | 113 | 111 |
| | | 25° C. | " | 120 | 117 | 112 | 109 |
| | | 37° C. | " | 90 | 60 | 50 | 30 |
| | Tetanus toxoid | 4° C. | 50.0 | 49.9 | 49.5 | 49.2 | 49.3 |
| | | 25° C. | " | 47.6 | 46.7 | 46.4 | 44.8 |
| | | 37° C. | " | 40.8 | 30.3 | 22.1 | 10.3 |
| Dried[2] | Pertussis toxoid | 4° C. | 14.0 | 13.8 | 13.5 | 13.3 | 13.2 |
| | | 25° C. | " | | 13.7 | 13.6 | 13.4 | 13.1 |
| | | 37° C. | " | | 13.5 | 13.4 | 13.2 | 13.0 |

TABLE 4-continued

| Form of adsorbed vaccine | Toxoid | Preservation temperature (°C.) | Titer (IU/ml) Preservation period (month) | | | | |
|---|---|---|---|---|---|---|---|
| | | | 0 | 6 | 12 | 24 | 36 |
| | Diphtheria toxoid | 4° C. | 125 | 128 | 125 | 121 | 119 |
| | | 25° C. | " | 122 | 117 | 115 | 114 |
| | | 37° C. | " | 125 | 124 | 118 | 112 |
| | Tetanus toxoid | 4° C. | 56.7 | 56.7 | 56.3 | 56.1 | 56.3 |
| | | 25° C. | " | 56.5 | 56.4 | 56.2 | 56.1 |
| | | 37° C. | " | 56.4 | 56.2 | 56.0 | 55.8 |

Note
(1)The vaccine obtained in Example 8.
(2)The vaccine obtained in Example 9.

APPLICATION EXAMPLE 2

(The safety, effectiveness and uniformity in quality of the present vaccines)

With respect to the safety and effectiveness of each of the present vaccines, the tests of safety and titer are conducted using mice and guinea pigs in accordance with the methods described in the Notification No. 159 of the Ministry of Health and Welfare of Japan as mentioned in Referential Examples 4, 5, 8 and 9. The uniformity in quality of the present vaccines is examined based on the weight ratio of F-HA to PT and the result of densitometry obtained in substantially the same manner as in Referential Example 9. As a result, it is found that the vaccines of the present invention are excellent in safety and effectiveness and are uniform in quality.

EXAMPLE 8

(Preparation of a diagnostic for pertussis)

A fraction of the purified pertussis antigen as obtained in Example 2 is adjusted to pH 8.6 and subjected to hydroxyapatite column chromatography to allow PT to pass through the column to recover a PT fraction. Then, the F-HA adsorbed on the column is recovered by elution using as an eluent a 1/20M phosphate buffer containing 1M NaCl to obtain an F-HA fraction. The antibody titers of the thus obtained F-HA and PT fractions are determined. The fractions are useful as a high purity diagnostic for detecting the infection of pertussis.

What is claimed is:

1. A method for culturing *Bordetella pertussis* which comprises culturing *Bordetella pertussis* at about 30°-37° C. for about 20-80 hours in a nutritent medium containing at least one substance selected from the group consisting of cellulose and cellulose derivatives at a concentration of about 0.01-2% by weight.

2. A method according to claim 1, wherein said cellulose derivatives are inorganic acid esters of cellulose, organic acid esters of cellulose and ethers of cellulose.

* * * * *